(12) United States Patent  
Johnson

(10) Patent No.: US 8,798,338 B2  
(45) Date of Patent: Aug. 5, 2014

(54) METHOD AND SYSTEM FOR COUNTING PARTICLES IN A LAMINAR FLOW WITH AN IMAGING DEVICE

(75) Inventor: Paul E. Johnson, Laramie, WY (US)

(73) Assignee: University of Wyoming, Laramie, WY (US)

( * ) Notice: Subject to any disclaimer, the term of this patent is extended or adjusted under 35 U.S.C. 154(b) by 1210 days.

(21) Appl. No.: 11/328,033

(22) Filed: Jan. 9, 2006

(65) Prior Publication Data

US 2007/0159627 A1   Jul. 12, 2007

(51) Int. Cl.  
*G06K 9/00* (2006.01)

(52) U.S. Cl.  
USPC .......................................... 382/128; 382/110

(58) Field of Classification Search  
CPC ................. G01N 15/1456; G01N 2015/1486; G01N 30/0005; G01N 15/1459; G01N 2015/149; G01N 15/1463  
USPC ............................... 382/128; 210/745; 356/73  
See application file for complete search history.

(56) References Cited

U.S. PATENT DOCUMENTS

| | | | |
|---|---|---|---|
| 4,112,301 A * | 9/1978 | Annis et al. .................... 250/364 |
| 4,814,868 A * | 3/1989 | James .............................. 348/83 |
| 5,030,002 A * | 7/1991 | North, Jr. ......................... 356/73 |
| 5,249,238 A * | 9/1993 | Komerath et al. ............. 382/107 |
| 5,978,435 A | 11/1999 | Christensen et al. |
| 6,115,119 A | 9/2000 | Sieracki et al. |
| 6,309,886 B1 | 10/2001 | Ambrose et al. |
| 6,573,696 B1 * | 6/2003 | Sahner .......................... 324/71.4 |
| 6,710,879 B1 | 3/2004 | Hansen et al. |
| 6,731,100 B1 | 5/2004 | Hansen et al. |
| 6,765,656 B2 | 7/2004 | Johnson |
| 7,422,693 B2 * | 9/2008 | Carter et al. ................... 210/745 |
| 8,384,897 B2 * | 2/2013 | Mizukami et al. ............. 356/335 |
| 8,471,220 B2 * | 6/2013 | Yamaguchi et al. ....... 250/458.1 |
| 8,541,759 B2 * | 9/2013 | Yamaguchi et al. ....... 250/458.1 |
| 2009/0218526 A1 * | 9/2009 | Shaw et al. .................... 250/574 |

* cited by examiner

*Primary Examiner* — Manav Seth  
(74) *Attorney, Agent, or Firm* — Jennifer L. Bales; Macheledt Bales LLP

(57) ABSTRACT

An invention is described which allows measurement of the concentration of fluorescent particles in a flowing (laminar) fluid by imaging the flow with a video camera. A beam of illumination is used to illuminate the target particles. Imaging optics are arranged to view the focal plane to form an image of the multiple fluorescent sample particles in the flow stream; a camera records the image formed by the imaging optics, and a counting algorithm enumerates the particles. Operational parameters of the system are adjusted according to an initial estimate of particle density, for example flow rate, exposure time, and sampling interval. In addition, the counting algorithm is selected according to the estimated particle density.

9 Claims, 10 Drawing Sheets

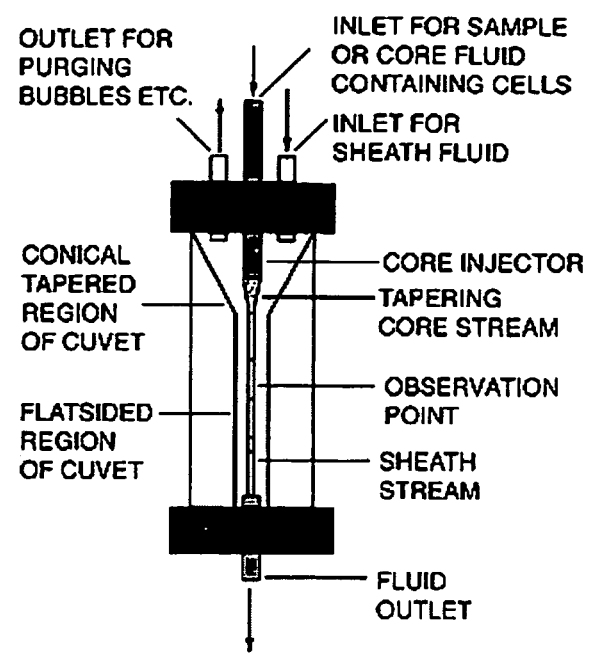
Figure 1 (Prior Art). *A typical flow cytometry system.*

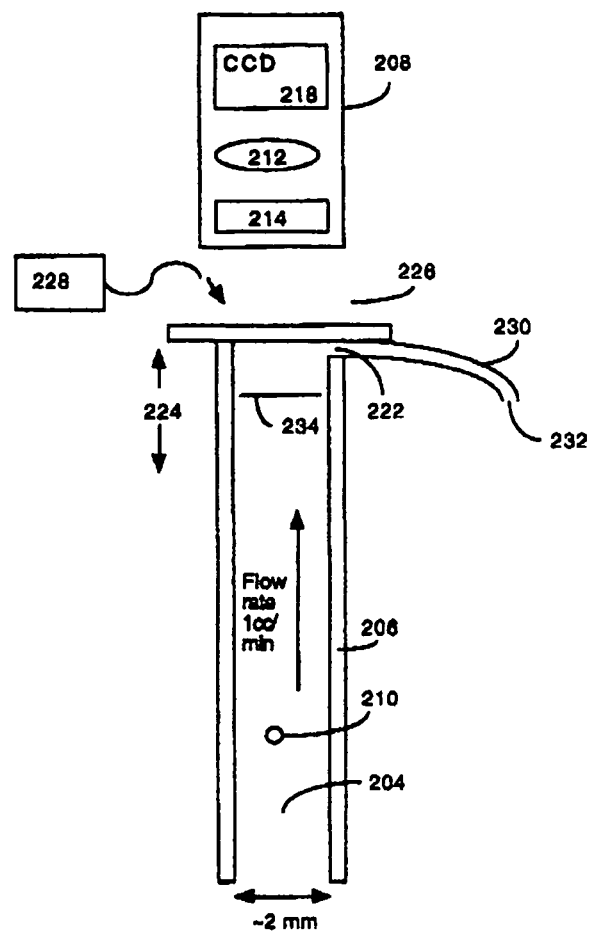
Figure 2 (Prior Art): *A schematic of the Fountain Flow system:*

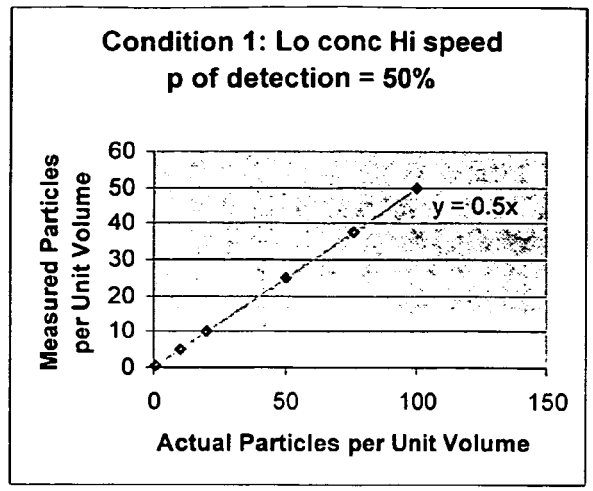
Figure 4: *Actual particle density vs. measured density where the probability of detection is 50% (equal to the slope of the line fit to the data).*
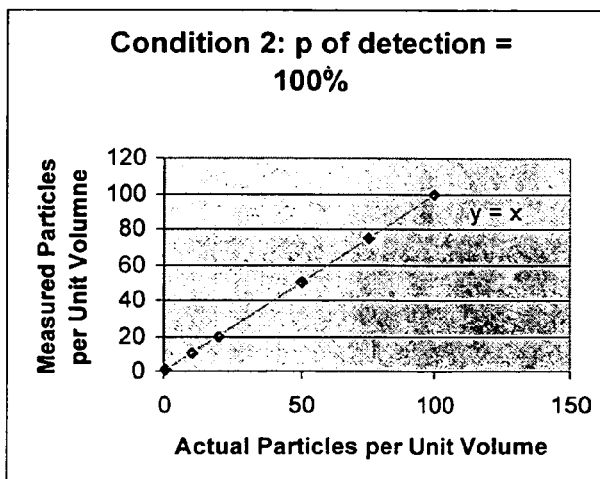
Figure 5. *Actual particle density vs. measured particle density where the probability of detection is unity, and there is no particle confusion.*

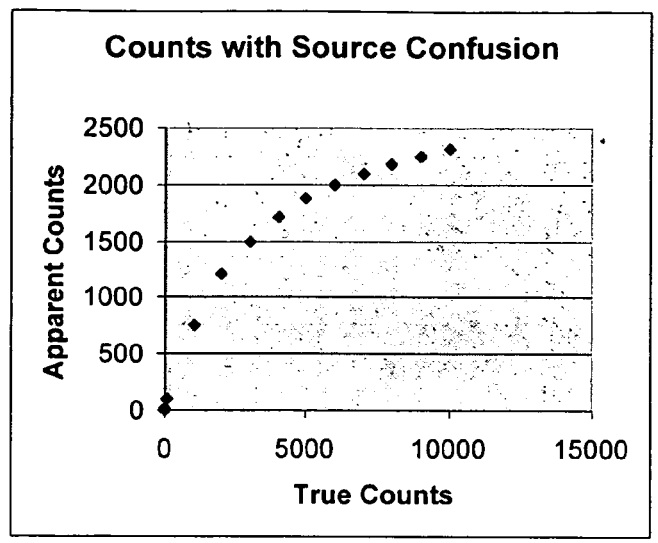
Figure 6. *Source confusion (for a single image) under Condition 3 for a 600x500 detector with confusion radius of 10 pixels.*

US 8,798,338 B2

METHOD AND SYSTEM FOR COUNTING PARTICLES IN A LAMINAR FLOW WITH AN IMAGING DEVICE

BACKGROUND OF THE INVENTION

1. Field of the Invention

The present invention relates to apparatus and methods for enumeration of specific target particles in a translucent or transparent flowing liquid. In particular, the present invention relates to counting of imaged particles wherein apparatus parameters and signal processing are adjusted according to estimated particle density in the flow.

2. Description of the Relevant Art

| Relevant U.S. Patents | | |
|---|---|---|
| 4,814,868 | March, 1989 | James |
| 5,978,435 | November, 1999 | Christensen et al. |
| 6,115,119 | September, 2000 | Sieracki et al. |
| 6,309,866 | October, 2001 | Ambrose et al. |
| 6,710,879 | March, 2004 | Hansen et al. |
| 6,731,100 | May, 2004 | Hansen et al. |
| 6,765,656 | July, 2004 | Johnson |

Relevant U.S. Patents

U.S. Pat. No. 4,814,868 March, 1989 James
U.S. Pat. No. 5,978,435 November, 1999 Christensen et al.
U.S. Pat. No. 6,115,119 September, 2000 Sieracki et al.
U.S. Pat. No. 6,309,866 October, 2001 Ambrose et al.
U.S. Pat. No. 6,710,879 March, 2004 Hansen et al.
U.S. Pat. No. 6,731,100 May, 2004 Hansen et al.
U.S. Pat. No. 6,765,656 July, 2004 Johnson Imaging and classification of low concentrations of selected target particles, cells in particular, in large volumes of fluid has a number of applications including: 1.) bioterrorism and biowarfare defense, 2.) food and water quality control, 3.) clinical detection of cancerous cells, and 4.) environmental monitoring. Cell imaging and counting systems developed to date usually suffer from: 1.) high cost, 2.) unsatisfactory sensitivity, 3.) slowness, 4.) large size, 5.) insufficient spectral and/or spatial resolution, and/or 6.) labor-intensive preparation steps.

Direct enumeration of cells may be accomplished using conventional flow cytometry. Flow cytometry is a commonly used technique to measure the chemical or physical properties of cells. Cells flow by a measuring apparatus in single file while suspended in a fluid, usually air or water. In immunofluorescence flow cytometry, cells can be identified by attaching fluorescent antibodies to each cell:

An antibody specific to the cell of interest is labeled with a fluorescent molecule or fluorochrome.
The labeled antibody is mixed in solution with the cells of interest. The antibodies attach to specific sites on the cells (called antigens).
The cells are passed in single file in a stream of liquid past a laser(s), which illuminates the fluorochromes and causes them to fluoresce at a different wavelength.
A photomultiplier or photodiode is used to detect a burst of fluorescence emission each time a marked cell passes in front of the detector.
The number of marked cells can then be counted. Antibodies can be chosen that are highly-specific to the cell(s) of interest.

Flow cytometry is currently used for a wide variety of applications including: measuring helper T-lymphocyte counts to monitor HIV treatment, measuring tumor cell DNA content in determining cancer treatment, and separating X- and Y-chromosome bearing sperm for animal breeding.

FIG. 1 (prior art) shows a typical flow cytometry system (from Shapiro, Practical Flow Cytometry, 2nd Edition). Putting flow cytometry into practice involves using two concentric cylindrical streams of fluid. The inner flow or core flow contains the cells to be sampled. The purpose of the outer stream or sheath flow is to reduce the diameter of the core flow. As the core and sheath fluids reach the tapered region of the flow, the cross-sectional area of the core flow is reduced. A small bore core flow (about 20 microns) allows for precision photometric measurements of cells in the flow, illuminated by a small diameter laser beam; all of the cells will pass through nearly the same part of the beam and will be equally illuminated. Why not just pass the cells through a small-bore transparent tube? Small diameter orifices are generally unworkable because they experience frequent clogging. All commercial flow cytometers now use a sheath/core flow arrangement.

Laser-induced fluorescence of fluorescent labels in a flow cytometer is a uniquely powerful method of making fast, reliable, and relatively unambiguous detections of specific microorganisms, such as foodborne pathogens. Several monographs describe the methods and applications of flow cytometry (e.g., Flow Cytometry: First Principles by A. L. Givan, 1992, and references therein).

Historically, flow cytometers have been very large, expensive laboratory-based instruments. They consume large amounts of power, and use complex electronics. They are not typically considered within the realm of portable devices. The size (desktop at the smallest), power requirements, and susceptibility to clogging (requiring operator intervention) of conventional flow cytometers precludes their use for many applications, such as field monitoring of water biocontamination.

U.S. Pat. No. 4,814,868 by James describes an imaging means for counting luminous particles in a boiler, but
 does not specifically apply to flow cytometry in general or Fountain Flow™ cytometry in particular,
 does not include a flow channel for entraining the particles,
 does not include an illumination device for exciting fluorescence in target particles,
 does not include a pumping mechanism, nor a way of controlling the pump rate,
 does not including a method for ensuring that particles are counted not more than once,
 does not provide for a means for counting measurements to be used to optimize system operational parameters on the fly,
 does not include a method for accurately counting particles by correcting counts for spatial confusion,
 does not include particle size as a counting criterion, and
 does not include the use of multiple counting algorithms based on particle density.

U.S. Pat. No. 6,309,886 by Ambrose et al. discloses an invention for the high throughput analysis of fluorescently labeled DNA in a transparent medium. This invention is a device that detects cells in a flow moving toward an imaging device. The flow is in a transparent tube illuminated in the focal plane from the side by a laser with a highly elongated beam. Although this invention does not suffer from the drawbacks listed above for alternative technologies, it is not suitable for applications where the flow medium is not transparent. It is also not an imaging technology, but rather a technology suitable for single-point photometric detection and characterization.

U.S. Pat. Nos. 6,710,879 and 6,731,100 by Hansen et al., disclose an invention for enumerating cells by flowing them into a relatively flat transparent chamber, exciting their fluorescence, and imaging the chamber in a single image with a camera. The camera image is digitized and the number of cells in the chamber enumerated.

U.S. Pat. No. 6,115,110 by Sieracki et al., discloses an invention for imaging cells, similar to the inventions by Hansen et al., in which samples are flowed into a flow chamber and imaged.

U.S. Pat. No. 5,978,435 by Christensen et al., discloses an invention in which liquid samples containing cells to be quantified to a specified uncertainty are measured one sub-sample at a time, until the desired uncertainty is achieved.

FIG. 2 (Prior Art) shows a schematic of a system, called the Fountain Flow Cytometer, described in detail in U.S. Pat. No. 6,765,656 by the present inventor (and incorporated herein by reference). Briefly:

A sample of fluorescently tagged cells (210) flows up the tube (206) toward the CCD/CMOS camera and foreoptics (208).

The cells are illuminated in the focal plane by a laser (228).

When the cell(s) pass through the CCD/CMOS camera focal plane (234) they are imaged by the CCD/CMOS camera (218) and lens assembly (212) through a transparent window, and a filter (214) that isolates the wavelength of fluorescent emission.

The fluid in which the cells are suspended then passes by the window and out the drain tube (230).

Normally the sample will flow upward, vertically. (In one embodiment, the sample would then flow out of a horizontal drain (230), from a channel (222) under a glass cover slip (220).) Volume 226 is filled with air, or transparent liquid, in our invention. This allows the illuminated volume (224) to be viewed without intervening solvent, decreasing the optical depth of the intervening fluid to near zero. The illuminated volume (224) is not required to be thin (i.e., it is not formed as a ribbon), nor does it have to be illuminated via laser. Illumination via incoherent light, such as a light-emitting diode, is not only acceptable, but in some ways is preferable, as this minimizes effects of interference on increasing the non-uniformity of the illumination in the illuminated volume.

The column of sample (206) is both viewed and illuminated end-on (one method of doing this is with a dichroic mirror allowing both the viewing path and illumination path to coincide with the flow axis, but in the opposite direction, similar to the optics in an epifluorescent microscope). The volume imaged will be controlled by the depth of field of the camera foreoptics, and will normally be kept small to prevent the negative effects of foreshortening on the resulting digital images. The ideal situation is where a particle flowing up the flow tube is imaged in a small number of pixels.

The cross-section of the flow tube that can be conveniently imaged is not dependent on the opacity of the sample fluid and can be very large (say a square of dimension 3 mm×3 mm) allowing an extremely high flow throughput of sample. We have achieved detections of amoebae with flow rates greater than 100 ml/minute using an 8-mm diameter circular Fountain Flow orifice, illuminated with an LED.

Because of slower flow of particles near the walls of the tube, particles near the walls may move more slowly and thus appear in multiple images and this effect will have to be taken into account when calibrating the device.

This invention, when combined with the use of fluorescent antibodies to selectively tag microorganisms, permits the detection of pathogenic microorganisms in food and water, just to name two applications. High-resolution images allow determination of the size of the fluorescently-tagged particles, allowing for screening based on size determination. It is possible to perform detection, enumeration, and size screening in real time. However, in order for this technique to be made practical for the accurate measurement of target particle density over a large dynamic range of particles densities, image processing means and counting means must be developed to:

attenuate slowly changing but relatively high intensity background from the video images, so that target particles can be discriminated from background, attenuate noise, detect particles based on sensitive and objective criteria, including the size and photometric intensity of candidate particles, reduce the effects of source confusion: i.e. correct for the statistical probability that two particles will appear close enough together in a single frame to be counted as one particle, count a particle once, even if it appears in more than one image, make an accurate measurement of the photometric intensity of each target particle and its size as it passes through the focal plane of the detector, and change the operational parameters of the system to adjust for the target particle density, on the fly, to extend the dynamic range of the system for measuring particle density. These operational parameters include flow rate, exposure time, illuminator brightness, and the algorithms used for image processing and counting.

A need remains in the art for improved apparatus and methods for high throughput imaging-based enumeration of specific particles in a translucent flowing liquid, wherein apparatus parameters and signal processing are adjusted according to estimated particle density in the flow.

SUMMARY OF THE INVENTION

It is an object of the present invention to provide improved apparatus and methods for high throughput imaging-based enumeration of specific particles in a translucent or transparent flowing liquid, wherein apparatus parameters and signal processing are adjusted according to estimated particle density in the flow.

Although one preferred embodiment of this technique is in conjunction with flow cytometry using the Fountain Flow invention of U.S. Pat. No. 6,765,656, it is not limited to this embodiment, and can be used for enumeration of target particles in any flow for which a cross-section of the flow is monitored by an imaging device with a focal plane that samples a cross-section of the flow. This would include conventional flow cytometry and the invention by Ambrose et al. (U.S. Pat. No. 6,309,886).

The invention as described here is a novel integrated system, comprising imaging device, illuminator, flow channel, image processing means for reducing background and noise, counting means for counting particles, analysis means for correcting the counts to accurately determine particle densities, and control means for adjusting the system parameters to optimize accurate measurements in a short time interval.

Some embodiments of the present invention provide apparatus and methods for high throughput, high sensitivity detection and identification of samples in a translucent or transparent flowing liquid. This is accomplished by providing a relatively large cross section axial flow, in which cells or other target particles suspended in a liquid are observed as they flow through the focal plane of the imaging device. Measuring target particle density over a wide dynamic range of densities is accomplished by allowing for adjustment of operational parameters of the system in real-time based on a quick measurement of target particle density.

The present invention has the advantages of solid-phase cytometry (Lemarchand et al., Aquat. Microb. Ecol., 25: 301-309, 200), including detection of individual microorganisms, at a much lower cost (<$10,000). This invention is based on taxonomic identification using fluorescent dyes, including immunofluorescent dyes. The detection steps include:

- An antibody specific to the cell species of interest is labeled with a fluorescent molecule or fluorochrome.
- The labeled antibody is mixed in solution with the cell species of interest. The antibodies attach to specific sites on the cells (antigens).
- The liquid suspension of cells is pumped in a flow channel toward a laser or LED, which illuminates the fluorochromes and causes them to fluoresce at a longer wavelength. Antibodies can be chosen that are highly specific to the cells of interest.
- A low-cost CCD (charge coupled device) or CMOS two-dimensional detector continuously images the flow channel so that it can image a flash of fluorescence emission each time a marked cell is illuminated by a laser diode or LED while passing through the focal plane of the detector.
- The number of marked cells is then counted via computer, and the results are used to optimize the operational parameters of the system for the density of target particles being measured.

The present invention includes apparatus and methods for imaging multiple fluorescent particles in a sample passing through a flow channel. In one preferred embodiment, a flow channel defines a flow direction for samples in a flow stream and has a viewing plane that bisects the flow. A beam of illumination is used to excite fluorescence from the target particles at the imager focal plane in the flow. Imaging optics are arranged to view the focal plane to form an image of the multiple fluorescent sample particles in the flow stream. A camera records the image formed by the imaging optics. A computer performs particle detection, enumeration, system control, and data analysis on the digital images recorded by the camera.

The imaging element may comprise a color filter, optics, and an imaging element such as a CCD or CMOS camera. The pumping element for maintaining the sample flow may consist of a syringe pump, peristaltic pump, or other computer controllable pump. The illumination may be provided by a laser or by an LED.

The present invention provides a method of enumerating particles in a flow wherein the flow is monitored by an imaging system including an imaging device having a focal plane that images an illuminated cross-section of the flow. The method comprised the steps of:
(a) imaging one or more frames with the imaging device;
(b) making a preliminary estimate of particle density, using a default counting algorithm, based upon an imaged frame;
(c) determining into which of two or more predetermined categories of density the particle density of the imaged frame falls;
(d) adjusting at least one of the following elements according to the determined density category—
  the counting algorithm,
  a parameter of the imaging system; and/or
  the flow speed; and
(e) enumerating particles in the flow after making the adjustment of step (c).

The adjusting step may adjust a parameter of the imaging system comprising exposure time or illumination intensity. Or, the adjusting step may adjust the counting algorithm by selecting between counting algorithms designed to operate at different particle density categories. Often the method measures the intensity distribution of particles, and adjusts the illumination intensity, the exposure time, and the pump speed according to the measured intensity distribution.

In the case where the counting algorithm is modified, the counting algorithms comprise at least a Lower Particle Density Algorithm and a High Particle Density Algorithm. The Lower Particle Density Algorithm implements the steps of differencing two successive image frames; flagging groups of pixels above a predetermined threshold of intensity; counting flagged groups as particles; and correcting counts for spatial confusion. Generally the step of counting particles uses size of a flagged group to discriminate particles. The step of correcting counts for spatial confusion generally will reduce the count according to a predetermined criterion based on distance between counted particles.

In a preferred embodiment, the High Particle Density Algorithm includes the steps of: flagging groups of pixels above a predetermined threshold of intensity; counting flagged groups as particles; and applying a spatial confusion correction factor to the count according to a formula based upon the count. Generally the process high pass filters the frames prior to the flagging step.

In a preferred embodiment, the Lower Particle Density Algorithm is further divided into a Low Particle Density Algorithm and an Intermediate Particle Density Algorithm. In this case, the Intermediate Particle Density Algorithm further includes the steps of determining which counted particles are likely to have been counted in previous frames, and decrementing the count accordingly. The Intermediate Particle Density Algorithm may also include the step of tracking the x,y coordinates of successive images in order to count a moving particle detected in successive frames as a single particle. The brightness of a particle detected in multiple frames may be taken to be it's maximum measured brightness.

The adjusting step may also adjust the exposure time and the sampling time of the imaging system as follows:
  for the Low Particle Density Algorithm the adjusting step sets the pump speed to high and the exposure time to long;
  for the Intermediate Particle Density Algorithm the adjusting step sets the pump speed to medium and the exposure time to medium;
  for the High Particle Density Algorithm the adjusting step sets the pump speed to low and the exposure time to fast.

In some cases the flow speed is adjusted such that substantially all of the particles within a predetermined volume of the flow will be detected in a single image. In some embodiments, the frame imaging step images frames in two colors, and further including the step of measuring each target particle for intensity in each of the two colors. The method may further include the step of measuring the brightness of imaged frames in a default state, and adjusting illumination or imaging system exposure time according to the measured brightness. If convenient, the enumeration step can be performed on a set of imaged frames after imaging has been completed, using data from the images to determine the enumeration algorithm.

Apparatus for enumerating particles in a flow according to the present invention includes:

(1) an imaging system for monitoring the flow including an imaging device having a focal plane that images an illuminated cross-section of the flow and captures one or more image frames;

(2) a processor for implementing the following modules:

a preliminary estimate module for estimating particle density, using a default counting algorithm stored within the processor, based upon an imaged frame from the imaging system;

a density categorizing module for determining into which of two or more predetermined categories of density the particle density of the imaged frame falls based upon the estimated particle density;

a control system module for generating a control signal to adjust a selected one or more of the following elements according to the determined density category—
(a) a counting algorithm stored within the processor,
(b) a parameter of the imaging system, and/or
(c) the flow speed, and an enumerating module for enumerating particles in the flow according to a counting algorithm after the element is adjusted; and (3) an adjusting unit for adjusting the selected element according to the control signal.

The processor may generate a control signal to adjust a parameter of the imaging system, in which case the adjusting unit changes the exposure time or illumination intensity of the imaging system according to the control signal. Or, the processor may generates a control signal to adjust the counting algorithm, in which case the adjusting unit would change the counting algorithm used by the enumerating module according to the control signal.

The imaging system may include a lens and wherein the imaging device comprises one of either a CCD imaging element, a CMOS imaging element, or a video camera. The flow may occur in a flow cytometer. The focal plane may substantially perpendicular to the flow direction, substantially parallel to the flow direction, or some other orientation. Often the flow speed is adjusted such that substantially all of the particles within a predetermined volume of the flow are detected in a single image frame. The apparatus may include either a syringe pump or a peristaltic pump with controllable flow rate for determining flow speed.

BRIEF DESCRIPTION OF THE DRAWINGS

FIG. 1 (Prior Art) is a schematic drawing illustrating a typical flow cytometry system.

FIG. 2 (Prior Art) is a schematic drawing illustrating a Fountain Flow cytometry system

FIG. 4 is a plot illustrating actual particle density versus measured particle density in low concentration, high flow speed conditions.

FIG. 5 is a plot illustrating actual particle density versus measured particle density in intermediate concentration, low flow speed conditions.

FIG. 6 is a plot illustrating actual particle density versus measured particle density in high concentration, low flow speed conditions.

DETAILED DESCRIPTION OF THE PREFERRED EMBODIMENTS

The present invention comprises apparatus and methods for counting particles in a flowing liquid. Both apparatus parameters and signal processing parameters are adjusted according to the concentration of particles in the flowing liquid.

Figure 3A:
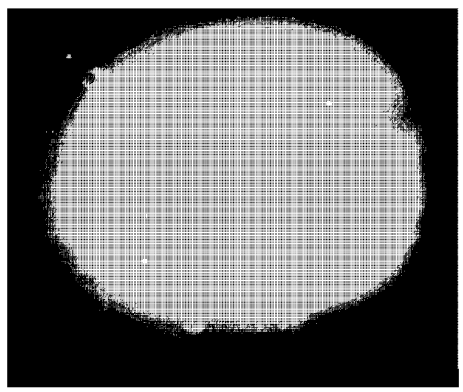
FIGS. 3A and 3B are successive images from a flow cytometer, with fluorescent target particles entrained in the flow, according to the present invention.
Figure 3B:
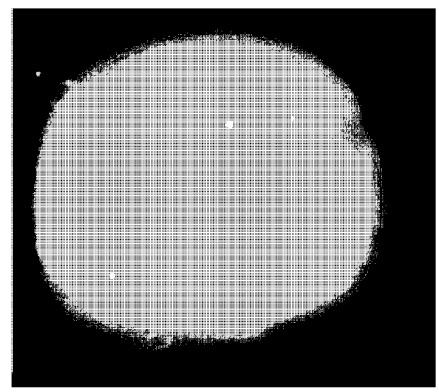
Figure 3C:
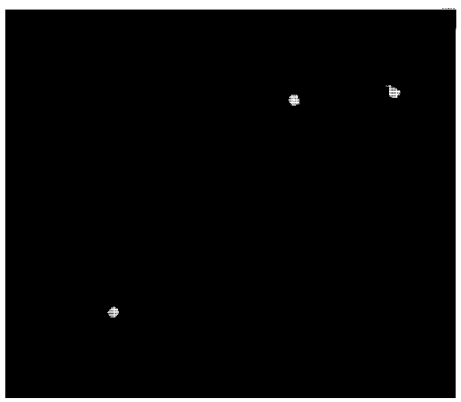
FIG. 3C shows the difference between the two images.

FIGS. 3A and 3B are successive images from a Fountain Flow Cytometer according to the present invention. FIG. 3C shows the difference between the two images. FIG. 3C illustrates the kind of figure that might result from algorithm 808A (for low particle density) or 808B (for intermediate particle density), since sequential image differencing is used, as described below in conjunction with FIGS. 9 and 10.

FIGS. 4, 5, and 6 illustrate how particle detection varies according to the particle concentration in the flow. At lower concentrations, each particle may be counted, whereas at higher concentrations, the number of actual particles must be estimated from the lower number of detected particles.

FIG. 4 is a plot illustrating actual particle density versus measured particle density in low concentration, high flow speed conditions, herein called Condition 1. There is a strong linear relationship between predicted and measured cell counts with a slope of approximately ½.

Condition 1 is the Condition where the flow rate is high enough so that particles reside in the illuminated focal plane for much less than the time it takes the camera to cycle through a single image, say 440 ms. For example, if a cell passes through the focal plane in <<440 ms, then the probability that it will be detected will be approximately the exposure time/440 ms, assuming that the cell residency time in the focal plane is large enough for detection. Under these conditions, an individual cell will not be detected in multiple frames. In this Condition, one is counting the actual number of cells flowing through the focal plane multiplied by the probability of making a detection (p). For some cameras/conditions, the cycle time is equal to the exposure time and the probability of making detection is unity. (Such is the case with CMOS imagers which allow continuous readout.) When the probability is one, Condition 1 and Condition 2 are identical.

FIG. 5 is a plot illustrating actual particle density versus measured particle density in intermediate concentration, low flow speed conditions (Condition 2).

Under Condition 2 there is a nearly linear relationship between predicted and measured cells counts with a slope of approximately 1, until source confusion begins to take hold at higher concentrations. Condition 2 is the Condition where the cell residency time in the illuminated focal plane is greater than or equal to the camera cycle time, and every cell passing through the image plane will be imaged at least once. In this Condition a correction must be made for cells imaged in multiple frames (spatial coincidences between frames). In addition, it is assumed that the concentration of cells in an individual image is low enough so that spatial coincidences within a single frame, i.e. source confusion, is not significant. Under Condition 2 one can measure the actual number of particles flowing through the focal plane by correcting for spatial coincidences among frames (counting as a single detection any cell in one frame that is seen at nearly the same coordinates in subsequent frames).

FIG. 6 is a plot illustrating actual particle density versus measured particle density in high concentration, low flow speed conditions (Condition 3).

Condition 3 is the Condition where the cell concentration within a single frame is large enough so that source confusion is significant. Spatial coincidences between frames are so large that they are ignored. This means that one is no longer measuring the actual number of cells flowing through the focal plane, as under Condition 1, but determining an empirical relationship between actual number of cells and cells counted. This determination could even be done in a series of snapshots of stationary calibration liquids of predetermined target particle density. In other words, a snapshot of a high concentration, stationary sample might yield hundreds of detections of cells in the focal plane. Snapshots of samples of differing concentrations would yield an empirical relationship between counts and actual concentration. Source confusion will affect this relationship.

Under Condition 3 there is a linear relationship between measured counts and actual counts only at concentrations not high enough to exhibit source confusion. The measured counts begin to saturate as source confusion becomes significant.

Figure 7:
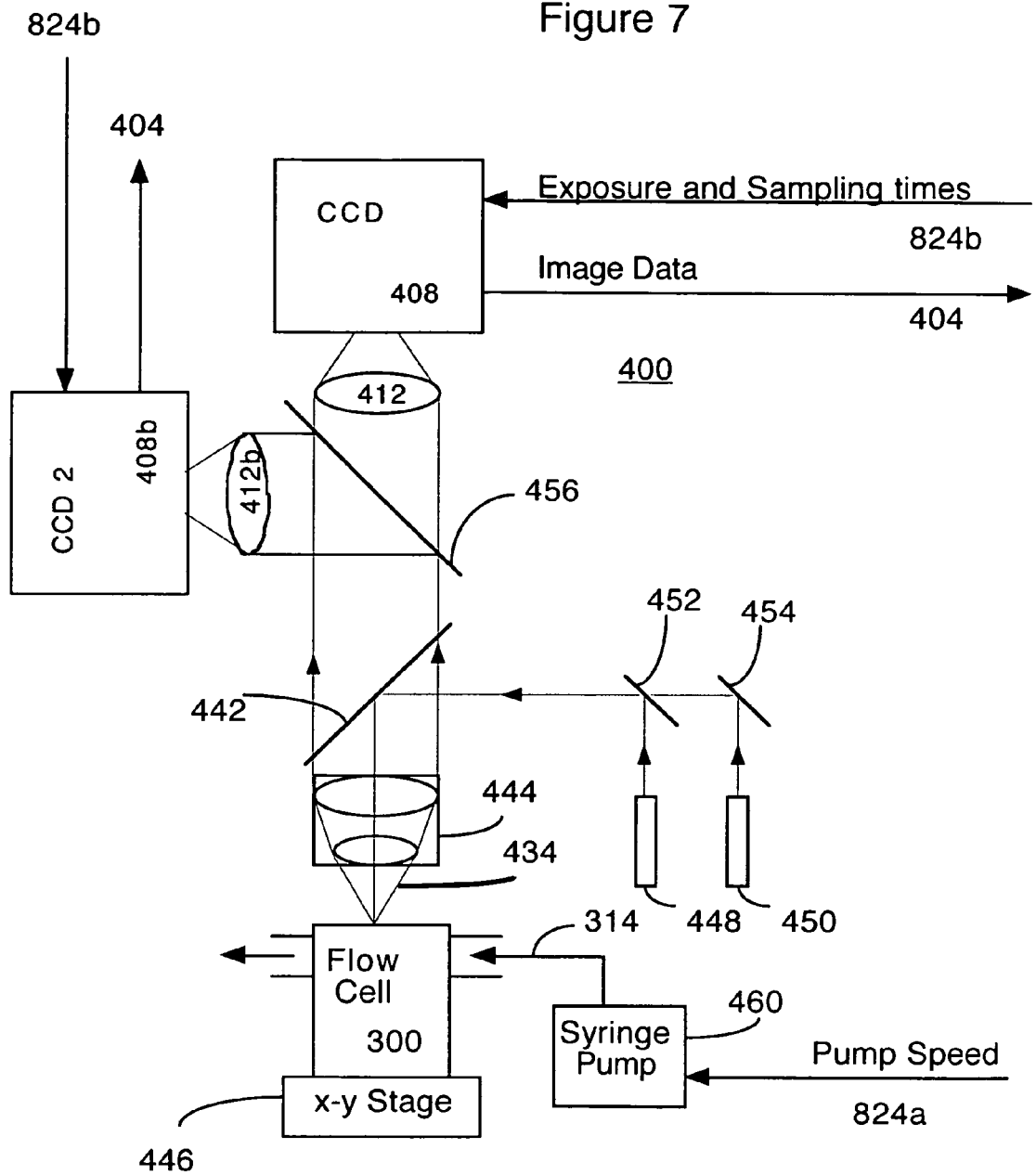
FIG. 7 is a block diagram illustrating a particle counting device according to the present invention.
Figure 8:
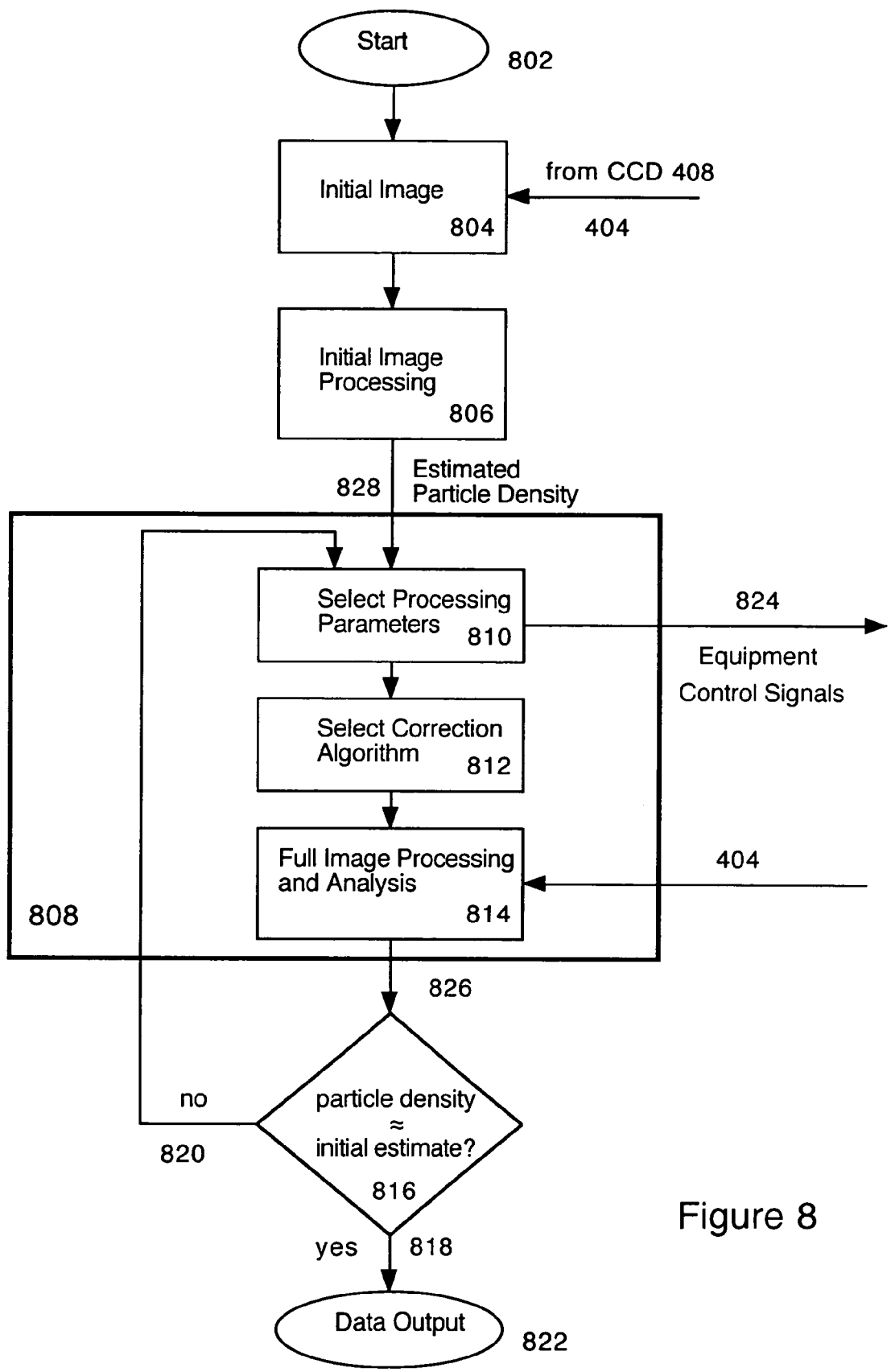
FIG. 8 is a flow diagram illustrating an overall process of particle counting according to the present invention.

FIG. 7 is a block diagram illustrating the elements of one embodiment of a particle counting device according to the present invention. FIG. 8 is a flow diagram illustrating the basic steps performed in the particle counting process. These two figures are discussed together, as there is a close relationship between them.

FIG. 7 is a block diagram illustrating an example of a particle counting device according to the present invention. The present example includes a flow cell arrangement, two illumination elements, and two imaging elements, but many other set ups are possible. Although the preferred embodiment illustrated in FIG. 7 is in conjunction with flow cytometry using the Fountain Flow invention of U.S. Pat. No. 6,765,656 and U.S. patent application Ser. No. 10/849,477 (both incorporated herein by reference), it is not limited to this embodiment, and can be used for enumeration of target particles in any flow for which a cross-section of the flow is monitored by a imaging device with a focal plane that samples a cross-section of the flow. This would include conventional flow cytometry and the invention by Ambrose et al. (U.S. Pat. No. 6,309,886).

In the embodiment of FIG. 7, a pump 460 causes the fluid to flow within flow cell 300. Lasers 448 and 450 illuminate the flow via optical elements 452, 454, 442, and 444. Light 434 emitted from the flow travels to CCDs 408 and 408b, via optical elements 444, 442, and 412, divided by beam splitter 456.

CCDs 408 and 408b provide image data to the image processing portion of the device, which processes the data as shown in FIG. 8. In turn, the processing portion adjusts apparatus parameters such exposure times, sampling times, and pump speed according to the particle density as determined by the processing portion.

*Escherichia coli* were detected by a Fountain Flow system according to the present invention, using the following parameters. The *E. coli* were detected using a SYBR Gold stain (Invitrogen, Eugene, Oreg.) while suspended in an aqueous solution. A 2-mm aperture was illuminated with an Argon ion laser with 22 mW of power at the flow aperture. Images were taken with Electrim 1000 L CCD camera through an Omega XF3105 filter.

Low density at these parameters was less than 10,000 cells per ml, with a flow rate of $8.33 \times 10^{-3}$ ml/s and a 100 ms exposure time. Intermediate density at these parameters was 10,000 to 100,000 cells per ml, with a flow rate of $1.17 \times 10^{-3}$ ml/s, and a 100 ms exposure time. High density at these parameters was greater than 100,000 cells per ml, with a flow rate of $5.83 \times 10^{-4}$ ml/s, and a 25 to 100 ms exposure time.

Those skilled in the art will appreciate that the particular particle densities, flow rates, and exposure times will vary according to the specific set-up and conditions. The invention is in determining the approximate particle density, and then varying the system parameters of the system to best enumerate the particles at that density.

FIG. 8 is a flow diagram illustrating an overall process of particle enumeration. Process starts in step 802. An initial image 404, from CCD 408 (See FIG. 7) is provided in step 804. Initial signal processing step 806 estimates the particle density in the initial image. Subprocess 808 comprises steps 810, 812, and 814, which vary according to the estimated particle density. See FIGS. 9-11.

Generally speaking, step 810 selects apparatus parameters, such as flow speed and exposure time, and provides these parameters to the flow-imaging equipment (see FIG. 7). Step 812 selects the correct image processing/particle counting algorithm for the present particle density environment (see FIGS. 9-11). Step 814 accomplishes full image processing and particle counting on images 404 from CCD 408 according to the selected algorithm. The results 826 are provided to step 816, which determines whether the particle density estimated in step 806 is close enough to the more accurate particle density found in step 814. If it is, 818, the particle data is output for use in step 822. If it is not, the new particle density count is provided to step 810 in a feedback loop 820, and more accurate results are obtained.

In a preferred embodiment of the present invention, an automated bacteria recognition and counting computer program counts bacteria from, for example, CCD/CMOS camera images.

Figure 9:
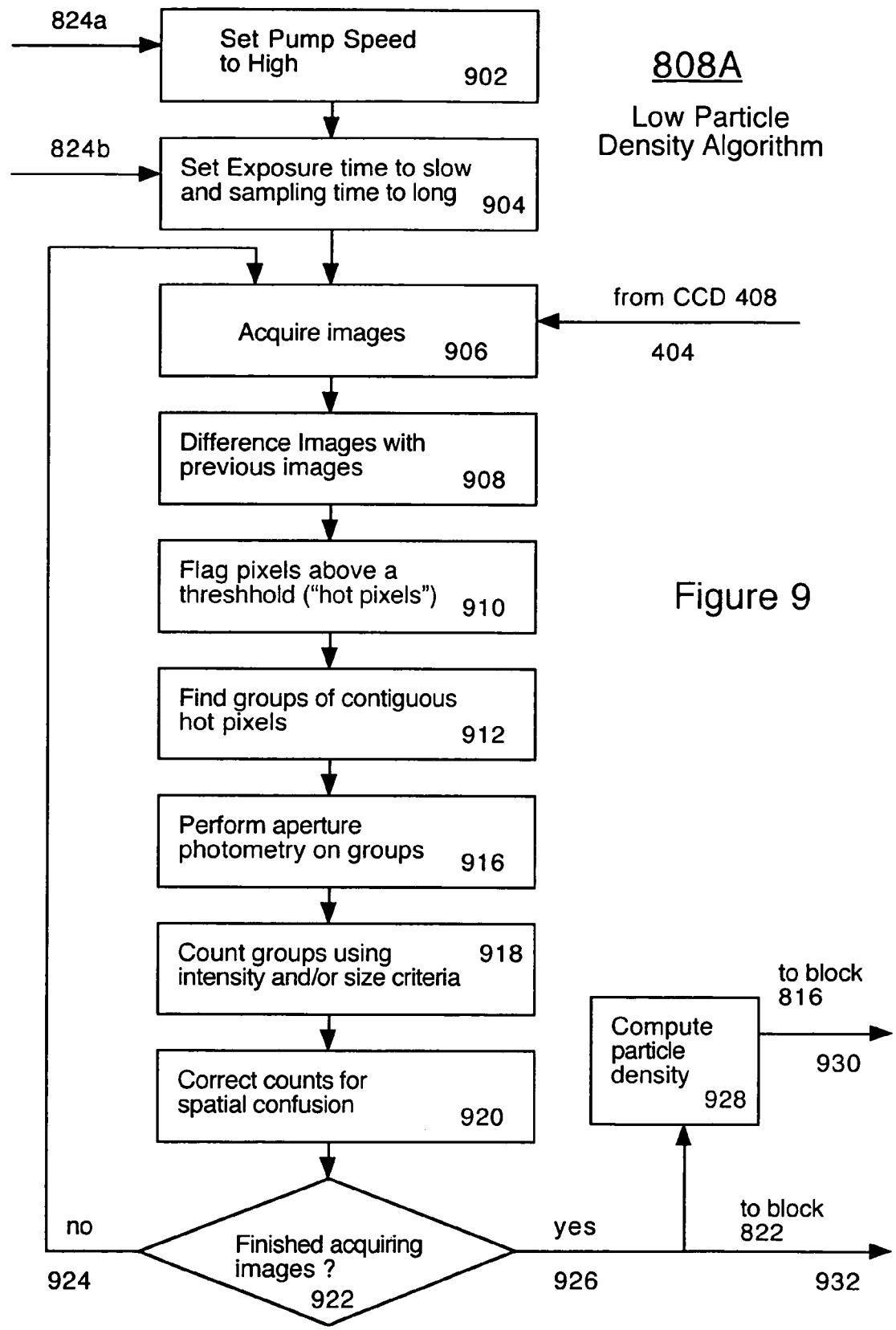
FIG. 9 is a flow diagram illustrating a specific algorithm utilized in the algorithm of FIG. 8 in low particle density conditions.
Figure 10:
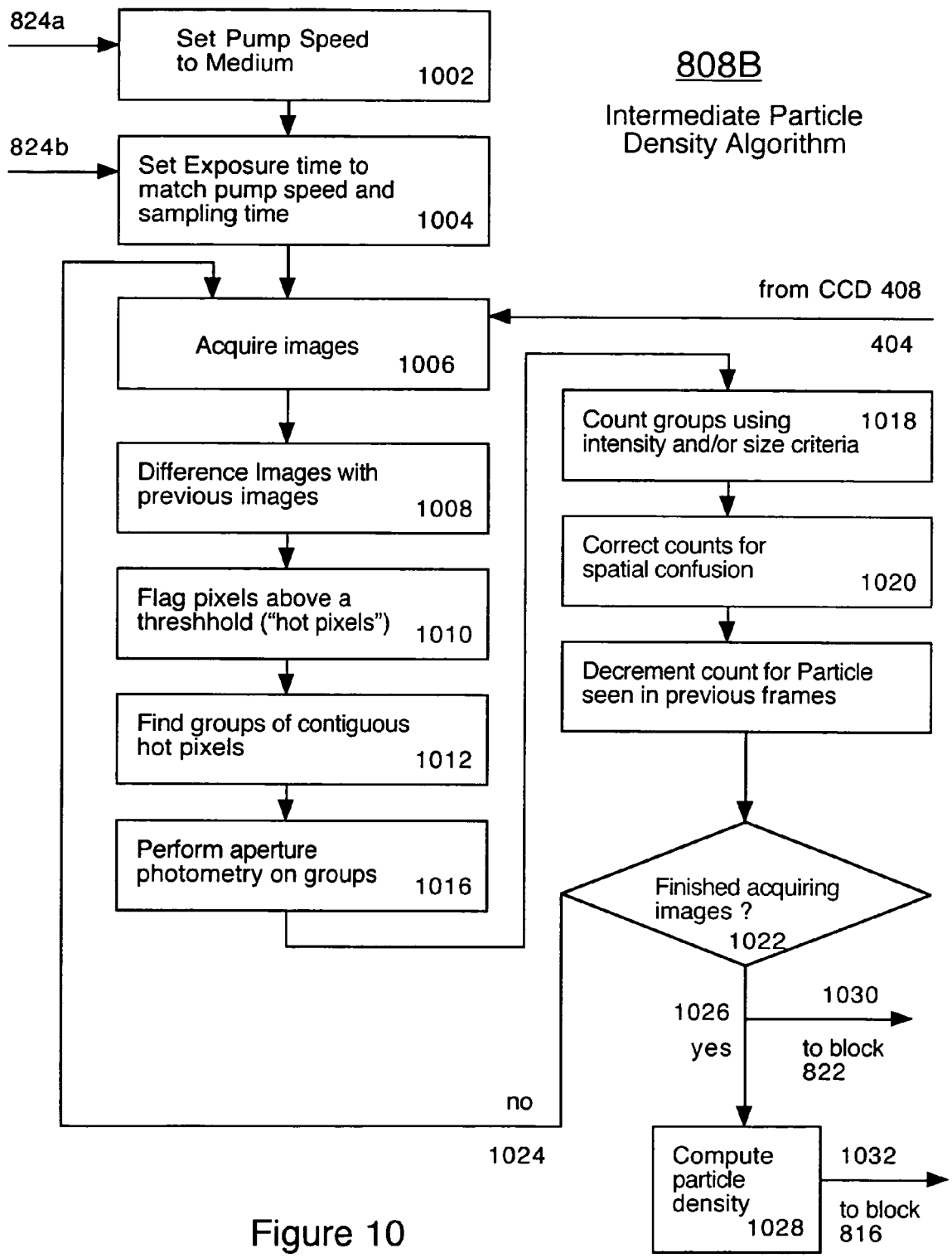
FIG. 10 is a flow diagram illustrating a specific algorithm utilized in the algorithm of FIG. 8 in intermediate particle density conditions.

The algorithm applied by the program is selected according to the particle density detected in the image. If a low particle density is detected, algorithm 808A, shown in FIG. 9, is used. If a medium particle density is detected, algorithm 808B, shown in FIG. 10, is used. If a high density of particles is detected, algorithm 808C is used. The low density and intermediate density algorithms eliminate the background by differencing two sequential images, and setting negative pixels to zero.

As the photometric background of the CCD images is non-uniform, owing to the non-uniform illumination of the Fountain Flow focal plane, background is eliminated in the program by differencing two sequential images, and setting negative pixels in the difference to zero (FIG. 3). Only target particles (e.g. bacteria) and noise remain in the difference image. Since target particles move laterally from one image to the next, a particle in one frame is not normally subtracted from a particle in a successive frame, except at high concentrations of bacteria.

As an example, the image differencing step of algorithms 808A and 808B queries the user for three parameters, listed in Table 1. The program then determines the median and standard deviation for each column in the image (as the CCD detector exhibits column-to-column fixed pattern offset). Next, the program identifies candidate bacteria pixels based on their signal strength above the noise. The program then identifies and counts candidate bacteria based on the number of detected candidate bacteria pixels in a single contiguous group and the total integrated photometric intensity within a specified radius of the center of the group. Such a program has been tested on a number of CCD images and the number of bacteria identified by eye is nearly equal to the number of bacteria counted by the program. Finally, the program compares the coordinates of bacteria found in successive images and determines which bright spots seen in successive images are probably the same bacterium (because their coordinates are within a predetermined distance).

Image differencing does not work well for images with high concentrations of bacteria. First, at high bacterial densities, it is not possible to accurately determine whether or not particles with similar x,y coordinates in successive images represent the same bacterium, or two bacteria that coincidentally share similar coordinates. This effect is called source confusion. Second, subtraction of one frame from the next can often subtract one bacterium from another in a successive image. For high bacterial concentrations, sequential image differencing is not performed. Algorithm 808C instead ignores intra-frame spatial coincidences of coordinates and does not correct for these. Algorithm 808C depends on developing an empirical relationship between measured Fountain Flow counts and counts from calibration samples. Algorithm 808C does not use sequential image differences to subtract background. Instead, median filtering is used to remove the broad background from point sources (bacteria) in the image. In other words, low spatial frequencies are removed from the data by application of a median filter (a 10×10 pixel square in one example).

TABLE 1

Criteria for the detection of a single bacterium. Each of the criteria below must be satisfied in order for a group of bright pixels to be classified as a single bacterium detection.

| | Criterion | Minimum Criteria for Bacterium Detection |
|---|---|---|
| 1. | # of standard deviations above the mean signal intensity for a pixel to be bright enough for group membership | ≥3 |
| 2. | # of continuous candidate pixels to be considered a group | ≥3 |
| 3. | photometric intensity of a group in order to be considered a bacterium | varies according to target bacterium, antibody, and label |

Figure 11:
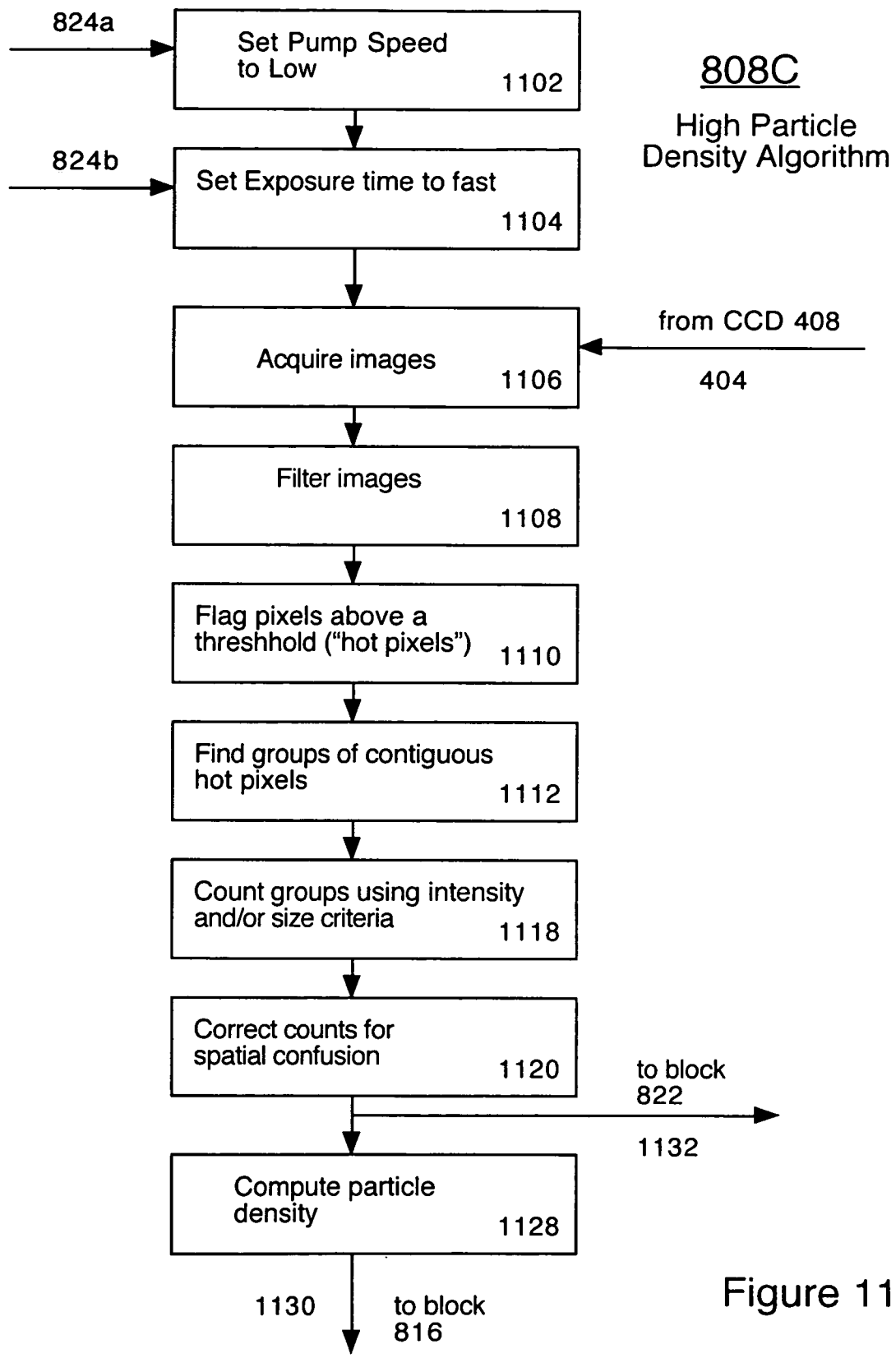
FIG. 11 is a flow diagram illustrating a specific algorithm utilized in the algorithm of FIG. 8 in high particle density conditions.

Thus, the present invention uses different algorithms for particle counting, depending upon the particle density of the image containing the particles. Ideally, apparatus parameters, such as flow speed and image exposure times, are also adjusted to optimize particle counting. FIG. 8 illustrates the overall particle counting algorithm of the present invention, while FIGS. 9-11 illustrate variations on particle counting tactics in different particle density conditions.

The sequence of tasks in measuring the density of target particles in a flow is given below. The sequence of imaging (data acquisition) can be performed simultaneously with the image processing, particle detection and counting steps given below, so that counts can be displayed during image acquisition, i.e. in real time. The preferred embodiment assumes the use of a Fountain Flow Cytometer as described in U.S. Pat. No. 6,765,656 by Johnson.

A preliminary particle count is accomplished in step 806. As an example, this process might include the following steps.

1. Pump at low speed (or with stationary flow) and take a "snapshot" (single image) of the flow.
2. Determine the mean (or median) and standard deviation for the image, or each column or row in the image. The latter is useful when there is a great deal of fixed pattern offset in the image that chiefly varies from column to column or row to row.
3. Median filter the image.
4. Count number of bright spots or streaks in the image composed of a minimum number of contiguous pixels, each with intensity greater than a chosen number of standard deviations above the mean (or median).
5. Compute the approximate intensity of each bright spot (or streak) by summing the intensity of all of the bright pixels comprising the spot.
6. Compute the concentration of target particles in the image (number of counts divided by the imaged volume, where imaged volume=depth of field×area of focal plane illuminated and imaged).
7. Use the density and intensity distribution of target particles to find the appropriate Condition number of the flow and the algorithms to be used for image processing, counting, analysis, and setting the optimum flow rate, exposure time, and illumination intensity.
8. Change operational parameters according to particle density.
9. Make final measurements using the appropriate algorithm 8A, B, or C.

FIG. 9 is a flow diagram illustrating a specific algorithm utilized in the algorithm of FIG. 8 in low particle density conditions. FIG. 10 is a flow diagram illustrating a specific algorithm utilized in the algorithm of FIG. 8 in intermediate particle density conditions. These algorithms both utilize image differencing to detect most or all of the individual particles in the flow.

Algorithm 808A, illustrated in FIG. 9 includes the following steps.

Step 902 sets the pump speed to high via control signal 824*a*. Step 904 sets the exposure time to slow and the sampling time to long via control signal 824*b*.

Step 906 acquires images, from a CCD 408 via data stream 404. A sequence of images is taken to allow determination of the target particle density to the desired accuracy.

Step 908 differences each image, by subtracting the previous image, to produce a series of images that are background subtracted. Negative pixels are set to zero to remove the effect of target particles from the image being subtracted.

Step 910 flags "hot" pixels, which are defined here as pixels above a certain threshold of brightness. Step 912 finds groups of pixels which contain a preselected minimum number contiguous hot pixels (which are hereafter called spots or bright spots), and determines the x,y image coordinates of the centroid of all of the detected spots.

Step 916 determines the brightness of each spot using aperture photometry.

Step 918 counts particles. This is the number of bright spots in image with intensity greater than a preselected threshold. The approximate intensity of each bright spot is computed by summing the intensity of all of the hot pixels comprising the spot. A more accurate measurement of intensity can be made using aperture photometry.

Step 920 corrects intra-frame spatial coincidences (i.e. correct for counting the same particle twice, by counting as one particle two or more spots, resulting from the same particle, detected within some predetermined radius).

In general, particle coordinates, particle intensities, and particle sizes are archived, and the original images are erased.

Step 922 determines whether all images have been gathered. If they have (926), then data 932 is output at block 822 (FIG. 8). Particle density 930 is computed in step 928 and output to block 816. If image acquisition is not complete (924), process returns to step 906.

Algorithm 808B, illustrated in FIG. 10 includes the following steps.

Step 1002 sets the pump speed to medium via control signal 824a. Step 1004 sets the exposure time and the sampling time to via control signal 824b. The pump 460 is operated at a rate that matches the camera cycle time: each particle is resident in the imaged volume so that it is seen for at least one complete camera exposure time, and at the same time will produce enough motion of the target particles to allow for identification in the difference of two successive images.

Step 1006 acquires a series of images, from CCD 408 via data stream 404. Step 1008 differences each image, by subtracting the previous image, to produce a series of images that are background subtracted. Negative pixels are set to zero to remove the effect of target particles from the image being subtracted.

Step 1010 flags hot pixels, and step 1012 finds groups of contiguous hot pixels, and determines the x,y image coordinates of the centroid of all of the detected spots.

Step 1016 determines the brightness of each spot using aperture photometry. Step 1018 counts particles, using intensity and/or size criteria. Step 1020 corrects intra-frame spatial coincidences.

Step 1021 decrements the particle count for particles seen in previous frames. If a particle is detected in multiple frames, the maximum brightness is recorded as the particle brightness.

Step 1022 determines whether all images have been gathered. If they have (1026), then data 1030 is output at block 822 (FIG. 8). Particle density 1032 is computed in step 1028 and output to block 816. If images acquisition is not complete (1024), process returns to step 1006.

FIG. 11 is a flow diagram illustrating a specific algorithm utilized in the algorithm of FIG. 8 in high particle density conditions. This algorithm is quite different than those for low and intermediate densities, because images cannot be differenced. The process proceeds as follows.

Step 1102 sets the pump speed to low via control signal 824a. Step 1104 sets the exposure time to fast and the sampling time to short (exposure time matched to pump speed and sampling time) via control signal 824b.

At high concentrations, a low pump rate is used and the focal plane is sampled with a small number of independent images (i.e. allowing sufficient time between exposures for the flow velocity to carry a particle across the depth of field).

Step 1106 acquires a series of images, from CCD 408 via data stream 404.

Step 1108 median filters the image to remove low spatial frequency background in the image.

Step 1110 flags hot pixels, and step 1112 finds groups of contiguous hot pixels, and determines the x,y image coordinates of the centroid of all of the detected spots. Step 1118 counts particles, using intensity and/or size criteria. Step 1120 corrects intra-frame spatial coincidences.

Data 1132 is output at block 822 (FIG. 8). Particle density 1130 is computed in step 1128 and output to block 816.

Particle density is computed in 1128 as number of counts divided by the imaged volume, where imaged volume=depth of field×area of focal plane illuminated and imaged. Then the measured particle density is corrected for source confusion (Equation 1 below).

Suppose that we look at a 600×500 image as being divided into 10×10 pixel superpixels, with 3000 such superpixels in an image. Assume that two cells found in the same superpixel will be confused, i.e. are close enough that they will be considered as one cell. When the image contains 1500 cell images, increasing the number of cells by one would mean a ~50% chance that this cell would not be detected owing to source confusion. Increasing the cell count further causes a non-linear response to cell concentration. Increasing the detector size from 600×500 to 1200×1000 obviously increases the dynamic range by a factor of 4.

This situation is similar to dead-time statistics in Geiger counters. Suppose that in our 60×50 superpixel array that we have counted n' pixels (apparent counts) in which a detection is made. There are n' "filled", or "dead" pixels (pixels in which a detection is made). The true number of counts should be n. The percentage of dead pixels are n'/3000. The number of coincidences or counts lost to two detections made in the same superpixel would be approximately n*n'/3000. The difference between true counts and apparent counts is then given by: n−n'=n*n'/3000. Or n=n'/(1−n'/3000). This is exactly the same as the dead-time formula. More generally:

$$n = n'/(1 - n'/(a/\Delta x \Delta y)) \qquad \text{Equation 1)}$$

where a is the number of detector pixels over which the imaged volume is imaged and $\Delta x$ and $\Delta y$ are the "discrimination lengths" in pixels (the minimum separation distance between two particle centroids in an image in order that they can be discriminated as two particles), in the x- and y-directions, respectively. The relationship between apparent counts and true counts in an image is shown in FIG. 6. This relationship can be used to better approximate the true cell density in the solution being measured. Also note that counting particles under Condition 3 extends the dynamic range of the device, as the relationship between true counts and apparent counts is non-linear.

The choice of algorithm for data analysis (Condition number) depends on flow speed, depth of field, exposure time, orifice size, detector format, and particle density, as given by Equations 2-4 below. If the number of particles in the imaged volume is small compared to $a/\Delta x \Delta y$ (Equation 1) then intra-frame source confusion is negligible. The number of particles in the imaged volume is equal to the imaged volume times the particle density. So the criterion for negligible source confusion (appropriate use of Condition 1 or 2) is given by Equation 2 for a "stationary" flow, i.e. where the time for a particle to transit the imaged volume is much less than the exposure time. Equation 2 is used when a "snapshot" of the flow is used to estimate n in order to determine which algorithm (Condition) to use.

$$n = \rho A d \ll (a/\Delta x \Delta y) \text{ negligible source confusion in a Stationary Flow,} \qquad \text{Equation 2)}$$

where n is the number of true counts in one frame, $\rho$ is the particle density, A is the cross-sectional area of the orifice, and d is the depth of field. If the inequality in Equation 2 is not satisfied, then Condition 3 holds; otherwise Conditions 1 or 2 are appropriate.

If the number of particles in the imaged volume at any instant in time is much smaller than the number of particles sweeping through the imaged volume during the exposure time, then the "Moving Flow" approximation of Equation 2a holds. This will generally be the case for Condition 1 and 2 flows. In addition, n=n' only for $n \ll (a/\Delta x \Delta y)$; otherwise a correction must be made using, Equation 1.

$$n = \rho A v \Delta t_{exp} (\text{for } n \ll (a/\Delta x \Delta y)) \text{ Moving Flow,} \qquad \text{Equation 2a)}$$

where v is the flow velocity and $\Delta t_{exp}$ is the camera cycle time. The camera cycle time, $\Delta t$, equals the length of an exposure, $\Delta t_{exp}$, plus the length of dead time between exposures, $\Delta t_{dt}$.

Whether or not Condition 1 or 2 is appropriate for measurements is determined by the minimum exposure time necessary for particle detection. If the residence time for a particle in the focal plane (depth of field/flow velocity) is less than or equal to the camera cycle time, then Condition 1 holds:

$$\Delta t_{exp} + \Delta t_{dt} \leq d/2v \quad \text{Condition 1.} \qquad \text{Equation 3}$$

The factor of _ in Equation 3 arises from the fact that particles are the focal plane. In the worst case for detection a particle will be seen for an equal period of time in two successive frames. In order to be sure that all particles have been exposed for the minimum length of exposure time, then the distance that a particle travels in a camera cycle time must be less than one-half the depth of field.

One objective is to minimize the sampling time. If we set the exposure time to the minimum acceptable time for detection of a target particle, $\Delta t_{min}$, then particle detection also requires that a particle must reside in the imaged volume for $\geq 2(\Delta t_{min} + \Delta t_{dt})$. This requirement in turn determines the maximum flow velocity, $v_{max}$, which permits detection of the particles in the flow (for Conditions 1 and 2):

$$v_{max} = d/2(\Delta t_{min} + \Delta t_{dt}) \text{ maximum flow velocity for Conditions 1 \& 2} \qquad \text{Equation 3a}$$

In general, the number of times a particle will be detected is k, where $$k = d/v(\Delta t_{exp} + \Delta t_{dt}) \text{ number of detections of a single particle.} \qquad \text{Equation 4}$$

If k>1 then Condition 2 holds; otherwise Condition 1 applies.

Those skilled in the art of particle enumeration will appreciate that the figures and description of preferred embodiments are useful for illustrating the present invention, but that many other configurations are also within the spirit of the invention. The heart of the invention is the concept of capturing image data, estimating the particle density in the images based on a default algorithm, and then adjusting apparatus parameters and/or the enumerating algorithm to do a more accurate count.

What is claimed is:

1. A method of enumerating particles in a flow wherein the flow is monitored by an imaging system including an imaging device having a focal plane that images an illuminated cross-section of the flow, the method comprising the steps of:
    (a) imaging one or more frames with the imaging device;
    (b) making a preliminary estimate of particle density, using a default counting algorithm, based upon an imaged frame;
    (c) determining into which of two or more predetermined categories of density the particle density of the imaged frame falls;
    (d) adjusting at least one of the following elements according to the determined density category—
        the counting algorithm;
        a parameter of the imaging system; and/or
        the flow speed; and
    (e) enumerating particles in the flow after making the adjustment of step (d);
    wherein the adjusting step adjusts the counting algorithm by selecting between counting algorithms designed to operate at different particle density categories;
    wherein the counting algorithms comprise a Lower Particle Density Algorithm and a High Particle Density Algorithm; and
    wherein the Lower Particle Density Algorithm implements the steps of—
        differencing two successive image frames;
        flagging groups of pixels above a predetermined threshold of intensity;
        counting flagged groups as particles; and
        correcting counts for spatial confusion.

2. The method of claim 1, wherein the step of counting particles further includes the step of using size of a flagged group to discriminate particles.

3. The method of claim 1 wherein the step of correcting counts for spatial confusion reduces the count according to a predetermined criterion based on distance between counted particles.

4. The method of claim 1 wherein the Lower Particle Density Algorithm is divided into a Low Particle Density Algorithm and an Intermediate Particle Density Algorithm, and wherein the Intermediate Particle Density Algorithm further includes the steps of determining which counted particles are likely to have been counted in previous frames, and decrementing the count accordingly.

5. The method of claim 4 wherein the adjusting step also adjusts the exposure time and the sampling time of the imaging system as follows:
    for the Low Particle Density Algorithm the adjusting step sets the pump speed to high and the exposure time to long;
    for the Intermediate Particle Density Algorithm the adjusting step sets the pump speed to medium and the exposure time to medium;
    for the High Particle Density Algorithm the adjusting step sets the pump speed to low and the exposure time to fast.

6. The method of claim 4 wherein the Intermediate Particle Density Algorithm includes the step of tracking the x,y coordinates of successive images in order to count a moving particle detected in successive frames as a single particle.

7. A method of enumerating particles in a flow wherein the flow is monitored by an imaging system including an imaging device having a focal plane that images an illuminated cross-section of the flow, the method comprising the steps of:
    (a) imaging one or more frames with the imaging device;
    (b) making a preliminary estimate of particle density, using a default counting algorithm, based upon an imaged frame;
    (c) determining into which of two or more predetermined categories of density the particle density of the imaged frame falls;
    (d) adjusting at least one of the following elements according to the determined density category
        the counting algorithm,
        a parameter of the imaging system; and/or
        the flow speed; and
    (e) enumerating particles in the flow after making the adjustment of step (d);
    wherein the adjusting step adjusts the counting algorithm by selecting between counting algorithms designed to operate at different particle density categories;
    wherein the counting algorithms comprise a Lower Particle Density Algorithm and a High Particle Density Algorithm; and
    wherein the High Particle Density Algorithm includes the steps of—
        flagging groups of pixels above a predetermined threshold of intensity;

counting flagged groups as particles; and applying a spatial confusion correction factor to the count according to a formula based upon the count.

8. The method of claim 7, further including the step of high pass filtering the frames prior to the flagging step.

9. The method in claim 6 wherein the brightness of a particle detected in multiple frames is taken to be its' maximum measured brightness.

\* \* \* \* \*